(12) United States Patent
An et al.

(10) Patent No.: US 8,283,622 B2
(45) Date of Patent: Oct. 9, 2012

(54) METHOD AND APPARATUS FOR TESTING MAGNETIC PROPERTIES OF MAGNETIC MEDIA

(75) Inventors: Chengwu An, Singapore (SG); Kaidong Ye, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 352 days.

(21) Appl. No.: 12/672,998

(22) PCT Filed: Aug. 13, 2008

(86) PCT No.: PCT/SG2008/000299
§ 371 (c)(1),
(2), (4) Date: Feb. 10, 2010

(87) PCT Pub. No.: WO2009/022993
PCT Pub. Date: Feb. 19, 2009

(65) Prior Publication Data
US 2011/0310387 A1 Dec. 22, 2011

Related U.S. Application Data

(60) Provisional application No. 60/935,433, filed on Aug. 13, 2007.

(51) Int. Cl.
*G01J 4/00* (2006.01)
(52) U.S. Cl. .................. 250/225; 250/559.09; 250/221; 324/244.1; 359/258; 356/369
(58) Field of Classification Search .................. 250/225, 250/559.09, 216, 222.1; 324/244.1, 210, 324/228, 244, 260; 359/246, 258, 280; 356/369
See application file for complete search history.

(56) References Cited

U.S. PATENT DOCUMENTS

| | | | |
|---|---|---|---|
| 4,816,761 A | | 3/1989 | Josephs |
| 5,034,679 A * | | 7/1991 | Henderson et al. ............. 324/96 |
| 5,736,856 A * | | 4/1998 | Oliver et al. ................ 324/244.1 |
| 6,501,269 B1 | | 12/2002 | Vajda |
| 2004/0066190 A1 | | 4/2004 | Ju et al. |
| 2006/0065820 A1 | | 3/2006 | Nagai |
| 2006/0250609 A1 | | 11/2006 | Meeks et al. |

OTHER PUBLICATIONS

Kryder et al., "Kerr Effect Imaging of Dynamic Processes", IEEE Transactions on Magnetics, 1990, pp. 2995-3000, vol. 26, No. 6.
Australian Patent Office, Written Opinion of the International Searching Authority, Oct. 28, 2008, issued in related PCT patent application No. PCT/SG2008/000299.
Australian Patent Office, International Preliminary Report on Patentability, May 28, 2009, issued in related PCT patent application No. PCT/SG2008/000299.
Australian Patent Office, International Search Report, Oct. 28, 2008, issued in related PCT patent application No. PCT/SG2008/000299.

* cited by examiner

*Primary Examiner* — Kevin Pyo
(74) *Attorney, Agent, or Firm* — Klarquist Sparkman, LLP

(57) ABSTRACT

A method and apparatus for testing a magnetic medium. The method comprises applying a magnetic field of a time-varying strength; directing a polarized optical beam towards a portion of the medium that is in the magnetic field, wherein the optical beam is reflected by a surface of the medium at a point of incidence in the magnetic field; moving the medium relative to the optical beam so as to cause the point of incidence to repeatedly traverse each of a plurality of sectors along a track on the surface; obtaining a series of Kerr signal measurements of the reflected optical beam; grouping measurements into ensembles such that the measurements in an individual ensemble are those obtained while the point of incidence was in a corresponding one of the sectors; and determining at least one magnetic property of at least one of the sectors from the measurements in the corresponding ensemble.

41 Claims, 10 Drawing Sheets

METHOD AND APPARATUS FOR TESTING MAGNETIC PROPERTIES OF MAGNETIC MEDIA

CROSS-REFERENCE TO RELATED APPLICATION

This application is the National Stage of International Application No. PCT/SG2008/000299, filed Aug. 13, 2008, entitled "METHOD AND APPARATUS FOR TESTING MAGNETIC PROPERTIES OF MAGNETIC MEDIA," listing Chengwu An and Kaidong Ye as the inventors, which claims the benefit under 37 U.S.C. 119(e) of U.S. Provisional Application No. 60/935,433, filed Aug. 13, 2007, to An et al., hereby incorporated by reference herein.

FIELD OF THE INVENTION

The present invention relates generally to the testing of magnetic media and, in particular, to a method and apparatus for dynamically testing magnetic properties of magnetic media including magnetic disks.

BACKGROUND

Magnetic media, such as computer hard disks, rely on magnetic properties to store data. To ensure that the disks meet certain standards of quality, these magnetic properties need to be tested from time to time, particularly during the manufacturing process.

Two important magnetic properties of interest include remanence and coercivity. Coercivity (typically expressed in oersteds) refers to the intensity of an applied magnetic field required to reduce the magnetization of a sample of ferromagnetic material to zero after the magnetization of the sample has been driven to saturation. For its part, remanence (typically expressed in ampere/m) refers to the magnetization left behind in the sample after an external magnetic field is removed.

The coercivity and remanence of a disk can be measured in the following way. A magnetic field is applied to the disk with a certain sweep rate from a positive value to a negative value and then back to its original positive value. A polarized laser beam is shone towards the disk surface at a point of interest that is subjected to the magnetic field. The beam is reflected by the disk surface. Due to what is known as the magneto-optic Kerr effect (MOKE), the reflected beam will undergo an amount of polarization rotation that depends on the magnetic properties of the disk surface. The component of the reflected beam exhibiting a changed polarization angle is known as the "Kerr signal". The Kerr signal is sampled many times during the sweeping of the magnetic field and a hysteresis loop is plotted from the acquired measurements. From this, the coercivity and remanence of the magnetic disk (at the point of interest) can be determined. To determine the coercivity and remanence of the magnetic disk at a second or subsequent point of interest on the surface of the disk, the disk position is changed and the process is repeated.

Since sweeping of the magnetic field takes several seconds, it is clear that testing numerous points of interest (e.g., different sectors of a track) can take minutes if not hours. This length of time for testing a single disk can be considered inefficient. Thus, there is a need in the industry for an apparatus and method for testing the magnetic properties of a magnetic medium by virtue of which multiple regions of the medium can be tested more efficiently.

SUMMARY OF THE INVENTION

In what will be described below in greater detail, there is provided a method for dynamically mapping magnetic coercivity and remanence of hard disk media using the magneto-optical Kerr effect described above. In this method, the magnetic disk is spun while an applied magnetic field is swept and a Kerr signal is being acquired. The overall effect is that the captured data is not just from one point but from a ring (track) which is subdivided into actual or conceptual sectors. The spin angle, the applied magnetic field and the sampling of the Kerr signal are all synchronized in phase. The acquired Kerr signal data is then segmented on a per-sector basis for each revolution, and the results for the same sector over multiple revolutions forms an ensemble. Each ensemble is then used to determine the coercivity and remanence of the concerned sector, and then a distribution of the coercivity and remanence for various sectors of the track is conveyed (e.g., graphically). The time taken for taking measurements for all sectors on one track (with each track consisting of multiple points along an arc length) is roughly the same time that would be required for taking measurements for just one point on the track in conventional approaches.

Accordingly, a first aspect of the present invention seeks to provide an apparatus for testing a magnetic medium, comprising:
  a magnetic field generation sub-system configured to apply a magnetic field of a time-varying strength to a portion of the magnetic medium;
  a light generation sub-system configured to direct a polarized optical beam towards the portion of the magnetic medium that is in the magnetic field, wherein the optical beam is reflected by a surface of the magnetic medium at a point of incidence in the magnetic field;
  a motion sub-system configured to move the magnetic medium relative to the optical beam so as to cause the point of incidence to repeatedly traverse each of a plurality of sectors along a track on the surface of the magnetic medium;
  a measurement sub-system configured to obtain a series of Kerr signal measurements of the reflected optical beam; and
  a control sub-system configured to group the series of Kerr signal measurements into ensembles such that the Kerr signal measurements in an individual ensemble are those obtained while the point of incidence was in a corresponding one of the sectors, the control sub-system being further configured to determine at least one magnetic property of at least one of the sectors from the Kerr signal measurements in the corresponding ensemble.

A second aspect of the present invention seeks to provide a method of testing a magnetic medium, comprising:
  applying a magnetic field of a time-varying strength to a portion of the magnetic medium;
  directing a polarized optical beam towards the portion of the magnetic medium that is in the magnetic field, wherein the optical beam is reflected by a surface of the magnetic medium at a point of incidence in the magnetic field;
  moving the magnetic medium relative to the optical beam so as to cause the point of incidence to repeatedly traverse each of a plurality of sectors along a track on the surface of the magnetic medium;
  obtaining a series of Kerr signal measurements of the reflected optical beam;
  grouping the series of Kerr signal measurements into ensembles such that the Kerr signal measurements in an individual ensemble are those obtained while the point of incidence was in a corresponding one of the sectors; and determining at least one magnetic property of at least one of the sectors from the Kerr signal measurements in the corresponding ensemble.

A third aspect of the present invention seeks to provide an apparatus for testing a magnetic medium, comprising:

means for applying a magnetic field of a time-varying strength to a portion of the magnetic medium;

means for directing a polarized optical beam towards the portion of the magnetic medium that is in the magnetic field, wherein the optical beam is reflected by a surface of the magnetic medium at a point of incidence in the magnetic field;

means for moving the magnetic medium relative to the optical beam so as to cause the point of incidence to repeatedly traverse each of a plurality of sectors along a track on the surface of the magnetic medium;

means for obtaining a series of Kerr signal measurements of the reflected optical beam; and means for grouping the series of Kerr signal measurements into ensembles such that the Kerr signal measurements in an individual ensemble are those obtained while the point of incidence was in a corresponding one of the sectors; and means for determining at least one magnetic property of at least one of the sectors from the Kerr signal measurements in the corresponding ensemble.

A fourth aspect of the present invention seeks to provide computer-readable media containing instructions which, when executed by a computing device, cause the computing device to implement a method that comprises:

receiving a time series of measurements, each measurement potentially representative of a manifestation of a magneto-optic Kerr effect within an individual sector from among a plurality of sectors of a magnetic medium;

grouping the time series of measurements into ensembles of groups of measurements, the groups from different ensembles being time-interleaved, wherein measurements potentially representative of the manifestation of the magneto-optic Kerr effect within an individual one of the sectors are distributed among the groups of measurements from within a same one of the ensembles;

determining at least one magnetic property of plural ones of the sectors from the groups of measurements in the corresponding ones of the ensembles; and outputting an indication of said at least one magnetic property of said plural ones of the sectors.

DETAILED DESCRIPTION

Embodiments of the present invention relate to the testing of magnetic properties of a magnetic medium containing regions on the surface of the medium where data is magnetically written to and read from. Such regions can be referred to as "tracks", and a "track" can be actually or conceptually subdivided into a plurality of "sectors". A non-limiting example of a magnetic medium that can be tested using embodiments of the present invention includes a computer hard disk.

Figure 1:
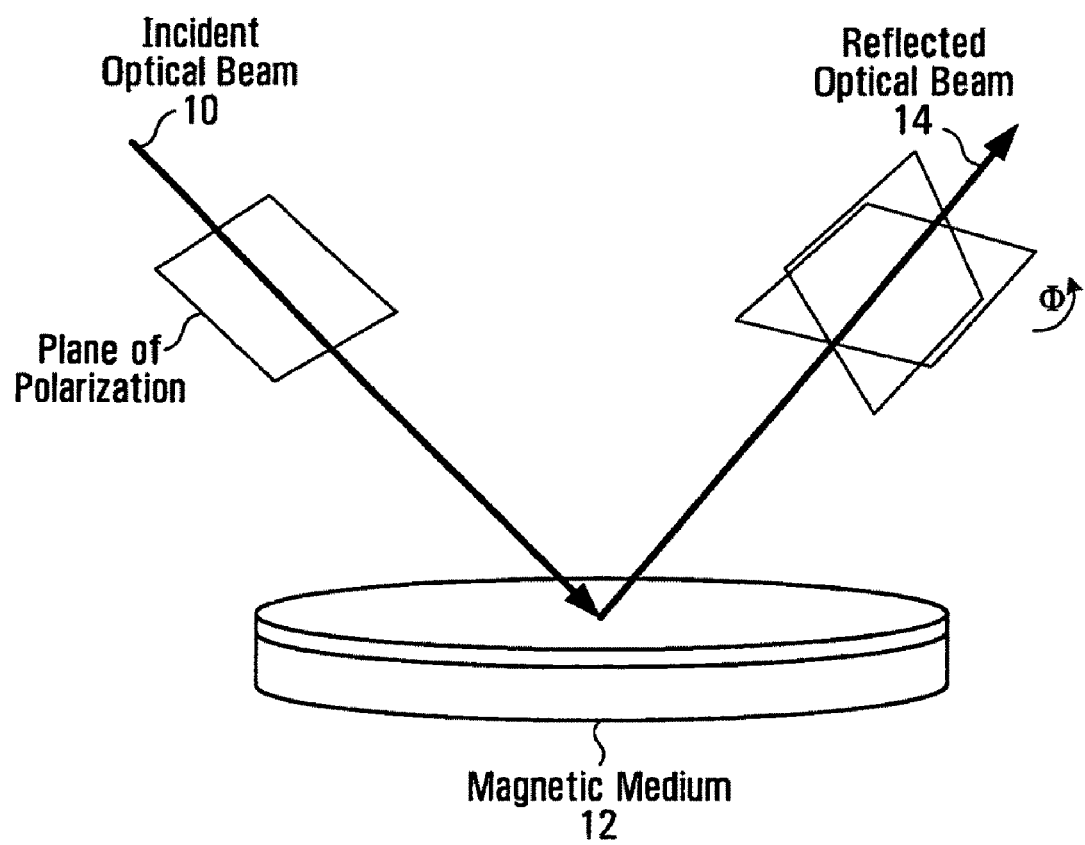
FIG. 1 conceptually illustrates the magneto-optic Kerr effect that takes place in a magnetic medium exposed to an externally applied magnetic field.

Before describing an embodiment of the invention in detail, it will be useful to briefly describe the general principle of what is known as the magneto-optical Kerr effect (MOKE), and schematically shown in FIG. 1. When an optical beam 10 exhibiting polarization in a "plane of polarization" is incident on a magnetic medium 12 under the influence of an applied magnetic field, the incident optical beam 10 is reflected by the magnetic medium, which results in a reflected optical beam 14 with a polarization in a plane that is rotated an angle of rotation of polarization relative to a reference orientation that would be exhibited in the absence of the applied magnetic field. The angle of rotation of polarization, denoted $\Phi$, is proportional by a factor f to the magnetization of the magnetic medium 12, where f is dependent on the magnetic medium itself.

Figure 2A:
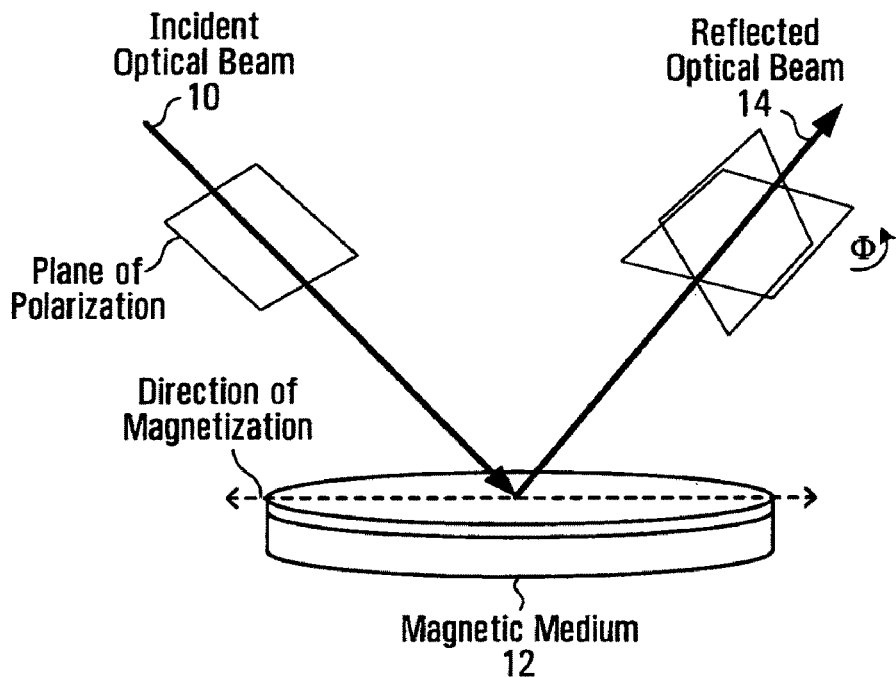
FIGS. 2A through 2C illustrate different types of magneto-optic Kerr effect depending on polarization direction of the magnetic medium.
Figure 2B:
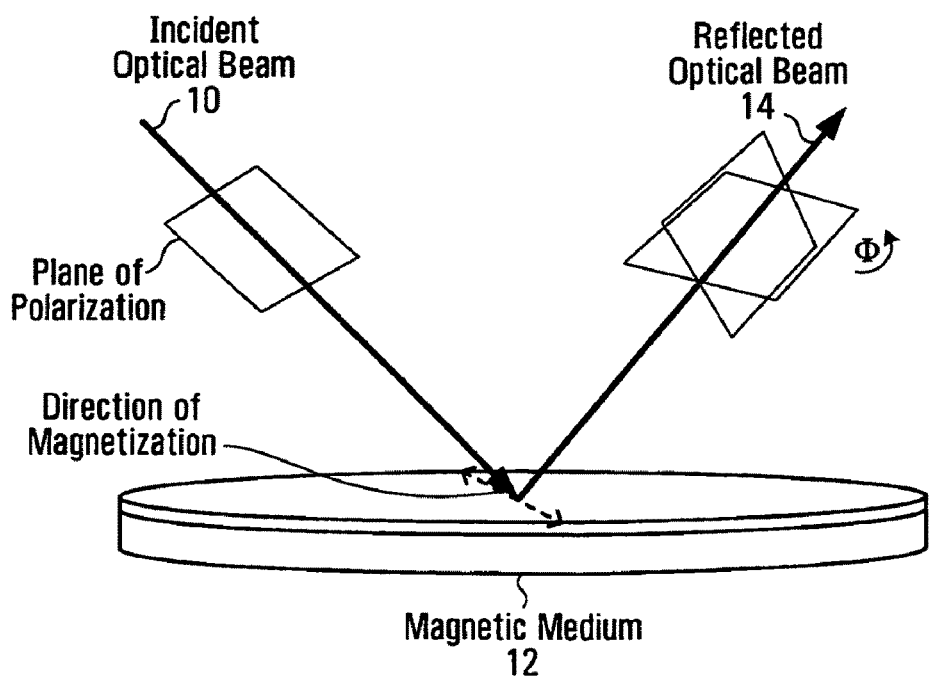
Figure 2C:
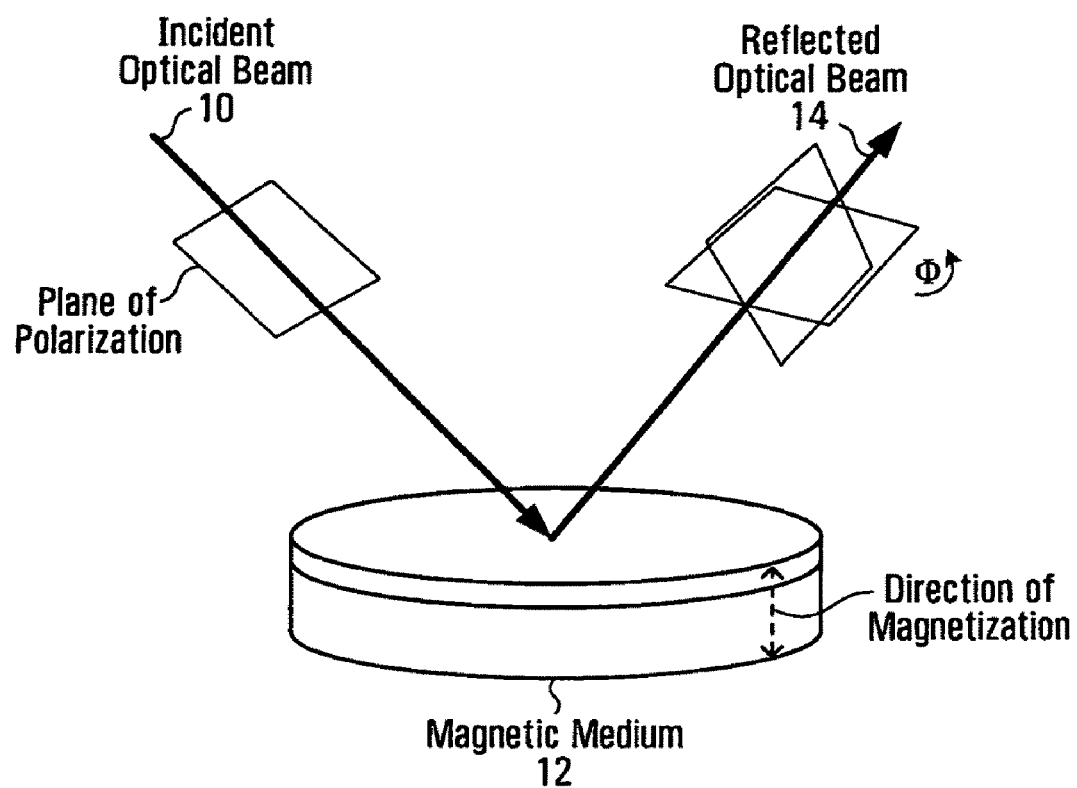

When the magnetization of the magnetic medium 12 is parallel to the surface of the magnetic medium 12 and in the plane of the incident optical beam 10 (see FIG. 2A), this produces a "longitudinal" Kerr effect. When the magnetization of the magnetic medium 12 is parallel to the surface of the magnetic medium 12 but orthogonal to the plane of the incident optical beam 10 (see FIG. 2B), this produces a "transverse" Kerr effect. When the magnetization of the magnetic medium 12 is orthogonal to the surface of the magnetic medium 12 and in the plane of the incident optical beam 10 (see FIG. 2C), this produces a "polar" Kerr effect.

Figure 3:
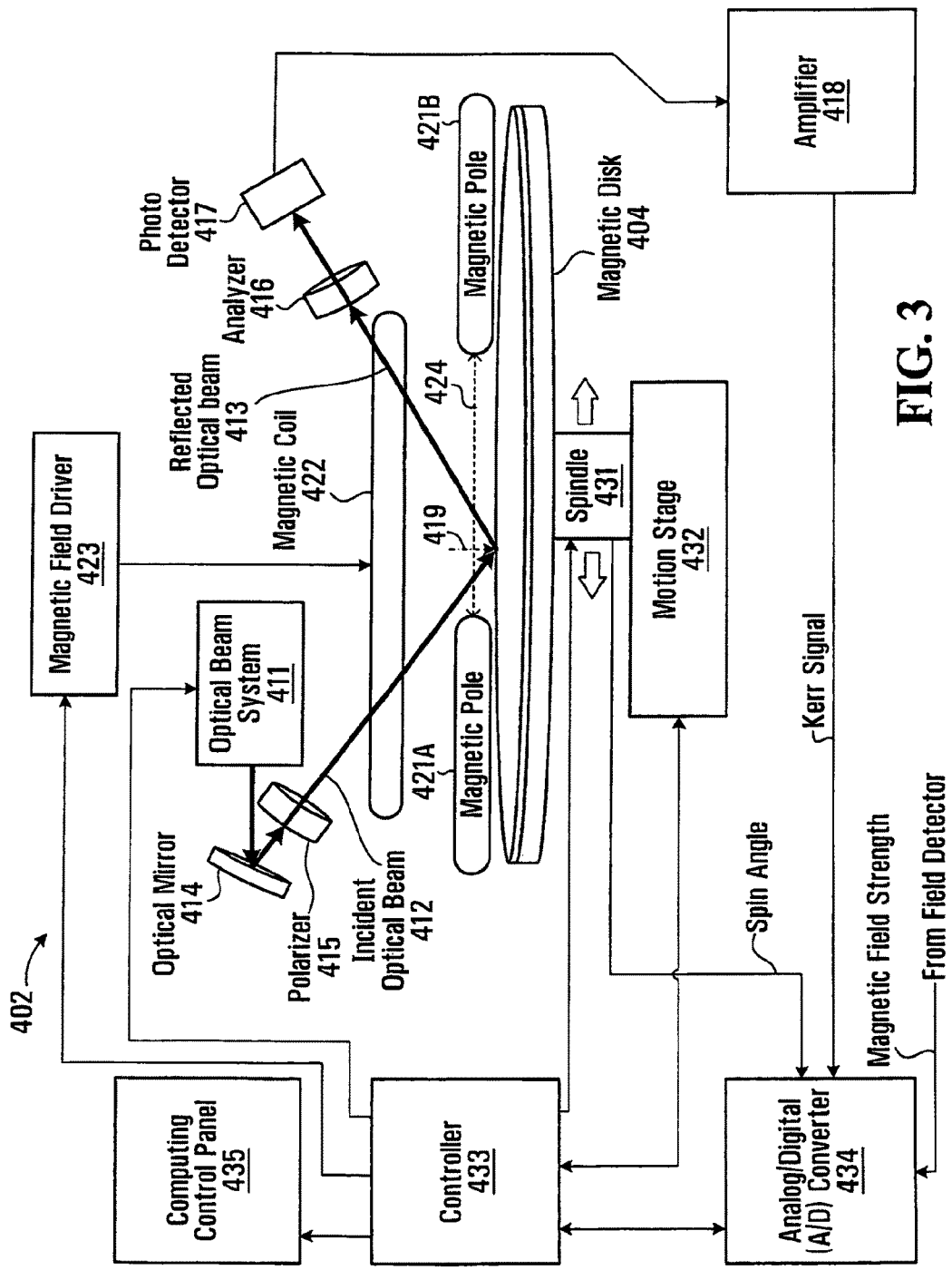
FIG. 3 is a block diagram of a test bed used to test a magnetic disk having multiple sectors, in accordance with a non-limiting embodiment of the present invention.

FIG. 3 is a block diagram of an apparatus (a "test bed") 402 that can be used for testing magnetic properties of a magnetic medium using the aforementioned magneto-optical Kerr effect in accordance with a specific non-limiting embodiment of the present invention. In the present non-limiting example, the magnetic medium being tested is a magnetic disk 404, however this should not be construed as limiting. The test bed 402 can perform an evaluation of the data recording and storage functionality of the magnetic disk 404, as characterized by certain magnetic properties (including coercivity and remanence).

The test bed 402 can be composed of the following subsystems that allow the detection and measurement of magnetic properties of a magnetic medium such as the magnetic disk 404:

a light generation sub-system for generating an incident optical beam 412 that results in a reflected optical beam 413 upon reflection by the magnetic disk 404;

a magnetic field generation sub-system that controls an orientation and a strength of a magnetic field applied at a given time to a portion of a track of the magnetic disk 404 (the "track under test"); and a motion sub-system that is used to control rotation of the magnetic disk 404 and the track under test;

a measurement sub-system for detecting a Kerr signal indicative of the angle of rotation of polarization Φ of the reflected optical beam 413;

a processing sub-system for acquiring the instantaneous values of the applied magnetic field, disk position and Kerr signal, grouping the measurements on a per-sector basis and processing the acquired values in order to obtain the magnetic properties of individual sectors of the track under test.

Further details regarding the individual components comprising these sub-systems, as well as an explanation of the operation of the test bed 402, are provided below in the context of a specific non-limiting embodiment of the present invention.

Light Generation Sub-System

The light generation sub-system includes an optical beam generation unit, which includes an optical beam system 411, an optical mirror 414 and a polarizer 415. The optical beam system 411 generates the incident optical beam 412, which is directed by an optical mirror 414 through a polarizer 415 onto a surface of the magnetic disk 404. The polarizer 415 imparts a polarization in a certain plane to the incident optical beam 412 before this beam reaches the surface of the magnetic disk 404 at a point of incidence 419. The point of incidence 419 identifies the area on the magnetic disk 404 where the incident optical beam 412 meets the surface of the magnetic disk 404 and is reflected as the reflected optical beam 413.

Magnetic Field Generation Sub-System

The magnetic field generation sub-system includes a magnetic field driver 423, a magnetic coil 422, magnetic poles 421A, 421B and an optional field meter (not shown). Generally speaking, the magnetic field generation sub-system is used to generate a magnetic field that is applied to a region of the magnetic disk 404. In particular, the magnetic field driver 423 determines the orientation and strength of the magnetic field to be applied for testing sectors on a particular track of the magnetic disk 404. Accordingly, the magnetic field driver 423 controls the signal imparted to the magnetic coil 422, thereby resulting in the creation of an magnetic field that is applied through the magnetic poles 421A, 421B and whose strength is measured and reported by the field meter, which is optional.

Figure 4A:
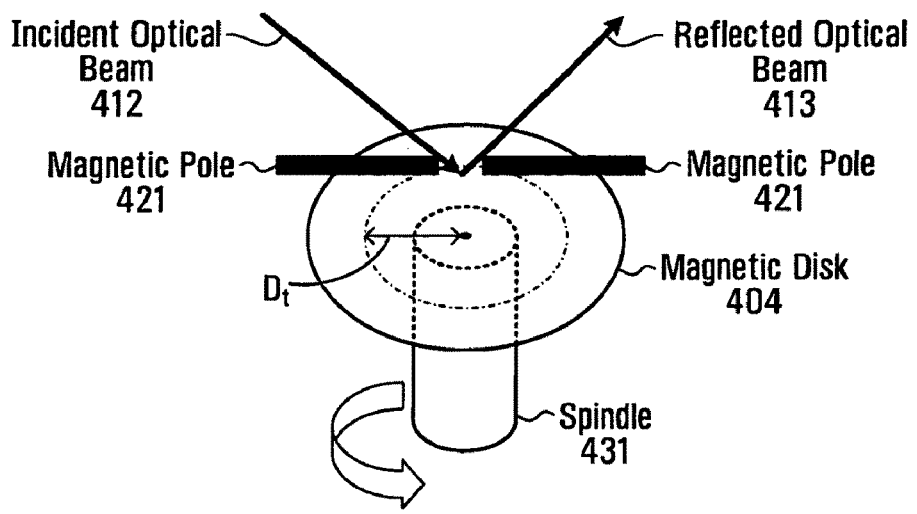
FIGS. 4A and 4B conceptually illustrate different orientations of a magnetic pole established by the applied magnetic field.
Figure 4B:
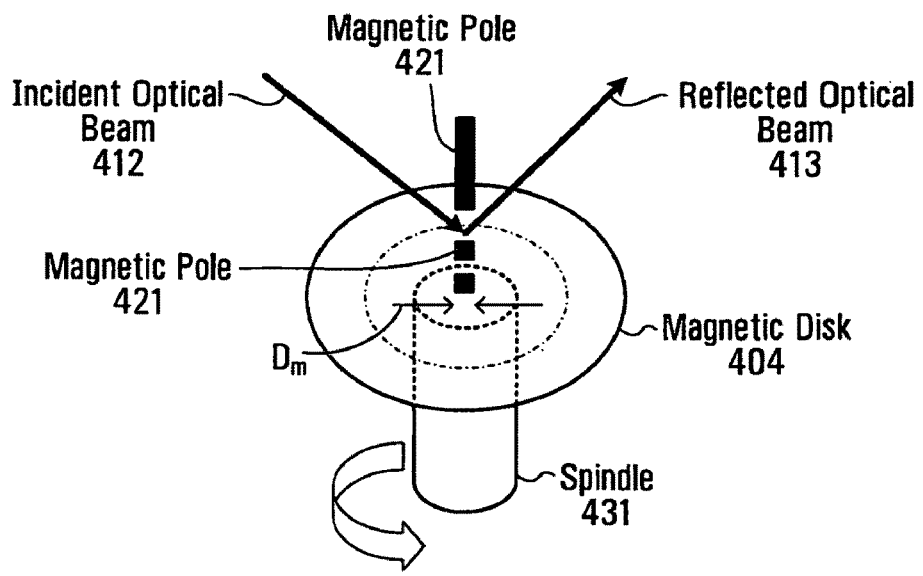

The magnetic poles 421A, 421B are proximate the surface of the magnetic disk 404 and are separated by a gap 424 of length $G_m$. The magnetic poles 421A, 421B may be oriented longitudinally or perpendicularly to the magnetic disk 404 so that the gap 424 is aligned for suitability with the recording properties of the magnetic disk 404. Reference is made to FIGS. 4A and 4B, which show two example orientations of the magnetic poles 421A, 421B relative to a magnetic medium. In FIG. 4A, the orientation of the magnetic poles 421A, 421B suitable for a longitudinal recording medium (such as a magneto-optical disk) is illustrated. In this case, the magnetic poles 421A, 421B are oriented parallel to a given track on one side of the medium so that magnetic field generated by the gap 424 covers several sectors of the given track. In FIG. 4B, the orientation of the magnetic poles 421A, 421B suitable for a perpendicular recording medium are illustrated.

In this case, the magnetic poles 421A, 421B are oriented perpendicularly to the magnetic medium so that the magnetic field generated by the gap 424 covers part of a given track located on both sides of the medium.

Motion Sub-System

The motion sub-system includes a motion stage 432 and a spindle 431 The motion stage 432 and the spindle 431 are connected to a controller 433 (in the processing sub-system, to be described later), which directs the spindle 431 to spin or stop and the motion stage 432 to acquire a desired lateral position. The spindle 431 is constructed in such a way that its rotation also rotates the magnetic disk 404, and contains a control mechanism connected to the processing sub-system that reports the spin angle of the spindle 431 (and hence the magnetic disk 404). The motion stage 432 is constructed in such a way that its movement translates the spindle 431 in a lateral fashion, which changes the track onto which the incident optical beam 412 is being shone, i.e., this selects the "track under test". The motion stage 432 may contain a control mechanism connected to the processing sub-system that reports the position of the track under test.

Measurement Sub-System

The measurement sub-system includes an analyzer 416, a photo detector 417 and an amplifier 418.

It will be appreciated that the magneto-optical Kerr effect rotates the polarization plane of the reflected optical beam 413 relative to the polarization plane of the incident optical beam 412, in dependence upon the magnetization of the sector in which the point of incidence 419 is located. The angle of rotation of polarization impacts how the reflected optical beam 413 travels through the analyzer 416 (which in a non-limiting embodiment may be implemented as a polarizer with a high extinction ratio). It should be noted that the optical axis of the analyzer 416 need not be perfectly aligned vertically to the optical axis of the polarizer 415. In fact, it is noted that when the applied magnetic field decreases from positive to negative, the angle of rotation of polarization of the reflected optical beam 413 will also decrease from positive to negative. If the polarizer 415 and the analyzer 416 are aligned sharply normal in their optical axes, the signal will become stronger no matter whether the rotation angle is positive or negative (i.e., no matter whether a positive or a negative magnetic field is applied). To reflect negative magnetization, an angle offset to the analyzer axis 416 can be useful, which guarantees that one direction of variation of the applied magnetic field, say positive, makes the signal stronger and another direction of variation of the applied magnetic field makes the signal weaker. This offset angle has an optimal range, which is about 4-10 times the maximal Kerr rotation angle, although offset angles outside this optimal range (or no offset angle) can be used without departing from the scope of the present invention.

The photo detector 417 converts the intensity of the signal at the output of the analyzer 416 into an analog electrical signal. The output of the photo detector 417 is then supplied to the amplifier 418, which increases the signal strength prior to sampling by the processing sub-system. The output of the amplifier 418 is hereinafter referred to as the "Kerr signal" and can be expressed in units of milli-degrees, or thousandths of a degree.

Processing Sub-System

The processing sub-system comprises the aforementioned controller 433, an analog-to-digital A/D converter 434 and a computing control panel 435.

Figure 9:
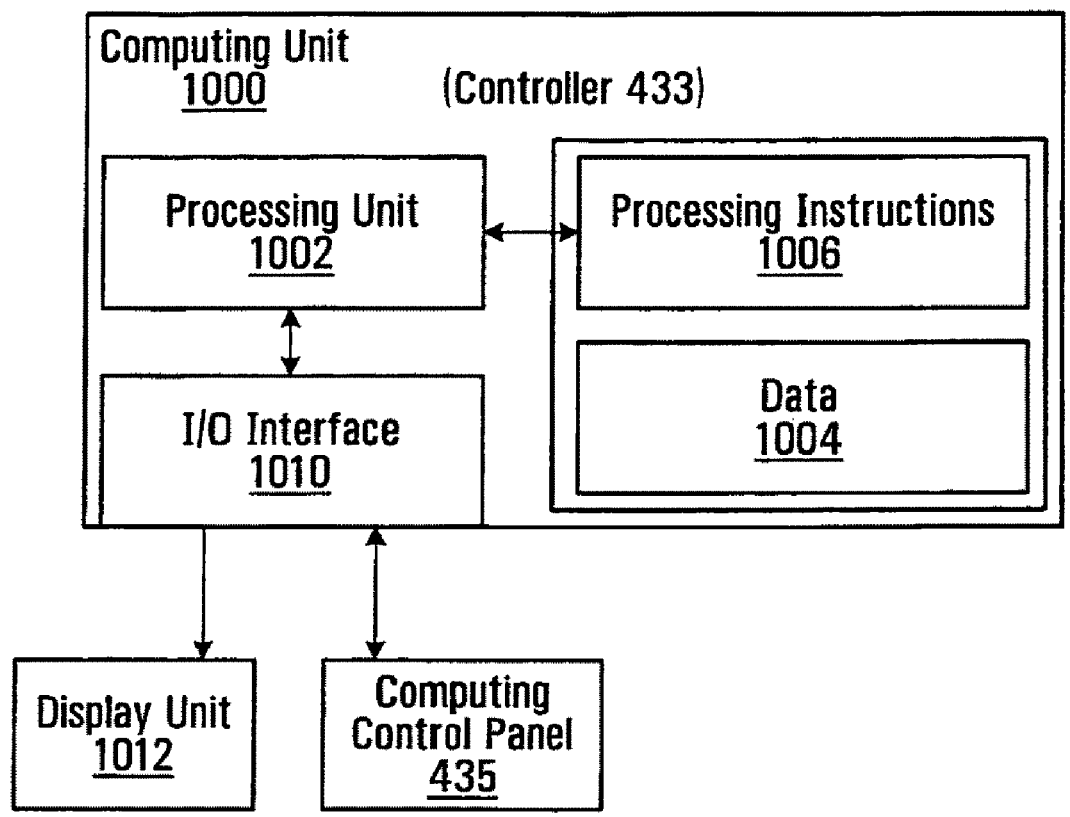
FIG. 9 illustrates a computing unit that can be configured to carry out processing operations and convey the graphical representations of FIGS. 8A and 8B.

The controller 433 may be configured as a computing unit 1000 of the type depicted in FIG. 9, which includes a processing unit 1002, data 1004 and program instructions 1006.

The processing unit 1002 is adapted to process the data 1004 and the program instructions 1006 in order to implement at least part of the functionality of the test bed 402. The program instructions 1006 may be written in a number of programming languages for use with many computer architectures or operating systems. For example, in some embodiments, the program instructions 1006 may be implemented in a procedural programming language (such as "V-C" or "V-B") or an object-oriented programming language ("Lab-view" or "JAVA", for example). The computing unit 1000 shown in FIG. 9 may be part of any suitable computing device including, but not limited to, a desktop or laptop computing device.

The computing unit 1000 may include an I/O interface 1010 for receiving data from, or sending data to, external components, such the spindle 431, the motion stage 432, the optical beam system 411, the magnetic field driver 423, the polarizer 415, the analyzer 416, the A/D converter 434 and so on. Additionally, the I/O interface 1010 can be used for receiving a control signal and/or information from a user (not shown) via the computing control panel 435, as well as for releasing a signal that drives a display unit 1012 and causes it to implement a user interface implemented by the program instructions 1006.

Optionally, the computing unit 1000 may include additional interfaces (not shown) for exchanging information with additional devices, such as a computer network connected via a wired or wireless interface (not shown).

The A/D converter 434 may have several channels for synchronous signal acquisition. For example, a first channel could produce samples of the instantaneous Kerr signal received from the amplifier 418, a second channel could produce samples of the instantaneous magnetic field strength reported by the field meter and a third channel could produce samples of the instantaneous spin angle reported by the spindle 431. The digital samples (measurements) output from the first channel form a "time series of Kerr signal measurements" that will be denoted $\{K(i)\}$. The digital samples (measurements) output from the second channel form a "time series of magnetic field strength measurements" that will be denoted $\{M(i)\}$. Finally, the digital samples (measurements) output from the third channel form a "time series of spin angle measurements" that will be denoted $\{A(i)\}$. The $\{K(i)\}$, $\{M(i)\}$ and $\{A(i)\}$ are stored in memory by the controller 433. The controller 433 processes the $\{K(i)\}$, $\{M(i)\}$ and $\{A(i)\}$ to determine the coercivity and remanence of the various sectors of the magnetic disk 404, as will be shown in further detail later on.

The computing control panel 435 acts as a user interface that allows a user to view and control the overall operation of the test bed 402. In particular, the computing control panel 435 is connected to the controller 433 and allows a user (not shown) to set and adjust certain parameters that will be used by the controller 433 during testing of the magnetic disk 404. For example, the user could use the computing control panel 435 to set the sampling rate of the A/D converter 434, rotation speed of the spindle 431, significant values and rate of change of the magnetic field (i.e., the magnetic field profile) to be applied by the magnetic field driver 423, the position of the track under test, the numbers of sectors that make up the track under test (as well as their position and arc length), etc. It is conceivable that the aforementioned parameters could be saved within the controller 433 in the form of a profile for a given type of magnetic medium. The user could recall this profile in order to use the test bed 402 to test similar media without having to set the parameters again. It should be understood that the computing control panel 435 may be implemented as a separate physical component connected to the controller 433 via a wired or wireless connection, or may be implemented as a graphical user interface by virtue of the program instructions 1006 within the controller 433.

Operation of Test Bed 402

With continued reference to FIG. 3, operation of the test bed 402 to test the magnetic disk 404 can now be described. A user (human or robotic) attaches the magnetic disk 404 to the spindle 431. The user then interacts with the computing control panel 435 to start the test bed 402, enters or recalls from memory any required parameters for the test (such as the rotation speed for the magnetic disk 404, the sampling rate of the A/D converter 434, the magnetic field profile, the position of the track under test, the number of sectors that make up the track under test, etc.), and initiates testing of the magnetic disk 404. Once the test is initiated by the user, the controller 433 activates the test bed's 402 constituent components.

Specifically, the controller 433 activates the motion stage 432 to move the spindle 431 and the magnetic disk 404 to the appropriate position for the track under test. In addition, the controller activates the spindle 431 to spin the disk 404. During testing, the rotation speed of the magnetic disk 404 is normally kept constant, although persons skilled in the art will appreciate that in some embodiments, the speed of rotation could be allowed to vary, as long as the speed versus time relation is known to the controller 433 and data acquisition synchronization is carried out by the program instructions 1006.

In addition, the controller 433 activates the magnetic field generation sub-system to apply a magnetic field to a portion of the track under test. Specifically, the magnetic field driver 423 energizes the magnetic coil 422 based on the strength and orientation of the magnetic field needed to generate a magnetic field. The magnetic field applied via the magnetic poles 421A, 421B (over the gap 424 of length $G_m$) magnetizes a portion of the track under test. During testing, the applied magnetic field is swept in accordance with the magnetic field profile selected by the user or stored in memory.

In addition, the controller 433 causes the light generation sub-system to shine a polarized beam of light onto the currently magnetized portion of the track under test. Specifically, the optical beam system 411 generates the incident optical beam 412 that is directed by the optical mirror 414 to pass through the polarizer 415 before reaching the surface of the magnetic disk 404 at the point of incidence 419. Naturally, the exact location of the point of incidence 419 within the track under test varies over time as the magnetic disk 404 rotates. Thus, where the track under test is actually or conceptually divided into a plurality of sectors, it will be seen that the point of incidence 419 traverses the various sectors over and over again as the magnetic disk 404 rotates.

The amplified output of the photo detector 417 (which captures part of the reflected optical beam 413 admitted by the analyzer 416) is sampled by the A/D converter 434, resulting in the time series of Kerr signal measurements $\{K(i)\}$. It is recalled that the Kerr signal is proportional to the magnetization of the magnetic disk 404 at the point of incidence 419.

Meanwhile, the output of the field detector (which indicates the instantaneous strength of the applied magnetic field) is sampled by the A/D converter 434; resulting in the time series of magnetic field strength measurements $\{M(i)\}$. It is recalled that the applied magnetic field follows a profile that can be user-defined or stored in memory.

In addition, the signal received from the spindle 431 (which indicates the instantaneous spin angle of the spindle 431) is sampled by the A/D converter 434, resulting in the time series of spin angle measurements $\{A(i)\}$. The spin angle will cycle repeatedly from 0 to 360 degrees as the magnetic disk 404 spins, and allows identification of which actual or conceptual sector contains the point of incidence 419 at a given sampling instant.

It should be appreciated that the sampling rate may be controllable and can be synchronized with a trigger signal. Specifically, the trigger signal can be received from the spindle 431 and indicates each new revolution of the magnetic disk 404. Alternatively, a clock signal can be introduced for timing the sectors. The clock signal is synchronously sampled by another channel of the A/D converter 434. For the case of 64 sectors, a clock signal of 256 periods per revolution of the spindle 431 could be set. This means that the acquired data in the time of the first 4 periods of the clock signal belongs to the first sector, the data acquired in next 4 periods belongs to the second sector, and so on, up to the $64^{th}$ sector. By tying the clock rate to the spin rate using this alternative approach, one may be able to achieve more reliable results, since measurements taken on the boundary between sectors are less likely to occur.

It should be appreciated that by controlling the sampling rate, the speed of rotation of the spindle 431 and the profile of the applied magnetic field, the controller 433 can ensure that at least a set minimum number of Kerr signal measurements K(i) is collected per actual or conceptual sector of the track under test and that the collected Kerr signal measurements K(i) are well distributed over the range of magnetic field strength measurements M(i) for those sampling instants.

Figure 5:
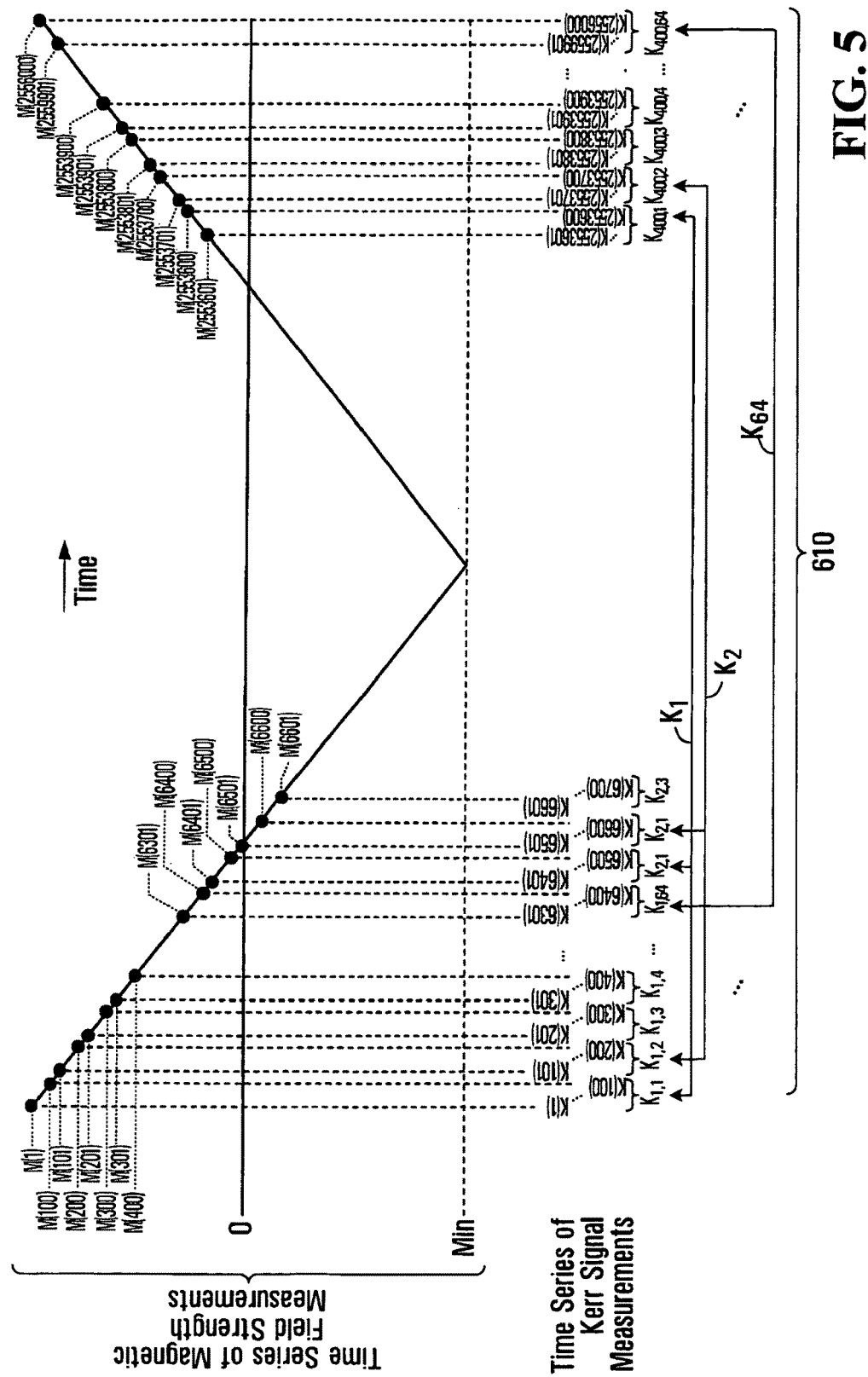
FIG. 5 shows a time series of measurements obtained by the test bed of FIG. 3 throughout the course of variation of the applied magnetic field.

More specifically, with reference to FIG. 5, let the track under test be divided into sixty-four (64) sectors, which can correspond to an actual distribution of sectors or can be a purely conceptual subdivision. The time series of Kerr signal measurements {K(i)} includes "ensembles" 610 of interleaved groups of measurements, where the $N^{th}$ ensemble (N=1, 2, ..., 64) is derived from Kerr signal measurements K(i) obtained from the reflected optical beam 413 while the point of incidence 419 was traversing the $N^{th}$ one of the sectors of the track under test. For example, the ensembles 610 that can be identified from the time series of Kerr signal measurements {K(i)} include an ensemble for sector #1 (denoted $K_1$), another ensemble for sector #2 (denoted $K_2$) and another ensemble for sector #64 (denoted $K_{64}$).

Similarly, the time series of magnetic field strength measurements {M(i)} includes interleaved ensembles 660, where the $N^{th}$ ensemble is derived from magnetic field strength measurements M(i) obtained (e.g., from the optional field meter) while the point of incidence 419 was traversing the $N^{th}$ one of the sectors of the track under test. For example, the ensembles 660 that can be identified from the time series of magnetic field strength measurements {M(i)} include an ensemble for sector #1 (denoted $M_1$), another ensemble for sector #2 (denoted $M_2$) and another ensemble for sector #64 (denoted $M_{64}$).

To identify which measurements in the time series {K(i)} (or {M(i)}) are associated with which of the ensembles 610 (or 660), the controller 433 considers the number of sectors of the track under test, the speed of rotation of the magnetic disk 404 and the sampling rate of the A/D converter 434. Where the sectors (actual or conceptual) are not contiguous and/or are not of equal arc length around the circular track, then adjustments need to be made in order to take these variations into account.

Consider now that the magnetic disk 404 turns at forty (40) revolutions per second with an applied magnetic field that sweeps from +10 kOe (ten thousand oersteds) to −10 kOe and back to +10 kOe in a loop lasting 10 seconds (i.e., a sweeping rate of 4 kOe per second). This means that the point of incidence 419 spends 0.390625 milliseconds on each sector, and returns to that sector every 25 milliseconds on a periodic basis. If the desired number of measurements to be taken within a single sector before the point of incidence 419 moves to the next sector is one hundred (100), then the sampling rate needs to be 256,000 measurements per second. It is also noted that the total number of revolutions is 400.

Recalling that the individual measurements in the time series of Kerr signal measurements {K(i)} are denoted K(i) (i=0, 1, ...), then the average Kerr signal measurement for the $p^{th}$ traversal (p=1, 2, ..., 400) of the $j^{th}$ sector (j=1, ..., 64) by the point of incidence 419 is denoted $K_{p,j}$, which is given by:

$$K_{p,j} = \sum_{i=(p-1)\times 6400+(j-1)\times 100}^{i=((p-1)\times 6400)+(j-1)\times 100+99} K(i)/100.$$

One can then form the Kerr signal ensemble for the $j^{th}$ sector, denoted $K_j$, by grouping together the average Kerr signal measurements $K_{p,j}$ for all 400 revolutions (p=1, 2, ..., 400) of the magnetic disk 404. In other words, $K_j = \{K_{p,j} | 1 \leq p \leq 400\}$. This is shown conceptually in FIG. 6 for the Kerr signal ensemble $K_1$, i.e., the Kerr signal ensemble for sector #1.

Recalling also that the individual measurements in the time series of magnetic field strength measurements {M(i)} are denoted M(i) (i=0, 1, ...), then the average magnetic field strength measurement for the $p^{th}$ traversal (p=1, 2, ..., 400) of the $j^{th}$ sector (j=1, ..., 64) by the point of incidence 419 is denoted $M_{p,j}$, which is given by:

$$M_{p,j} = \sum_{i=(p-1)\times 6400+(j-1)\times 100}^{i=((p-1)\times 6400)+(j-1)\times 100+99} M(i)/100.$$

One can then form the magnetic field strength ensemble for the $j^{th}$ sector, denoted $M_j$, by grouping together the average magnetic field strength measurements $M_{p,j}$ for all 400 revolutions (p=1, 2, ..., 400) of the magnetic disk 404. In other words, $M_j = \{M_{p,j} | 1 \leq p \leq 400\}$. This is shown conceptually in FIG. 6 for the magnetic field strength ensemble $M_1$, i.e., the magnetic field strength ensemble for sector #1.

Figure 6:
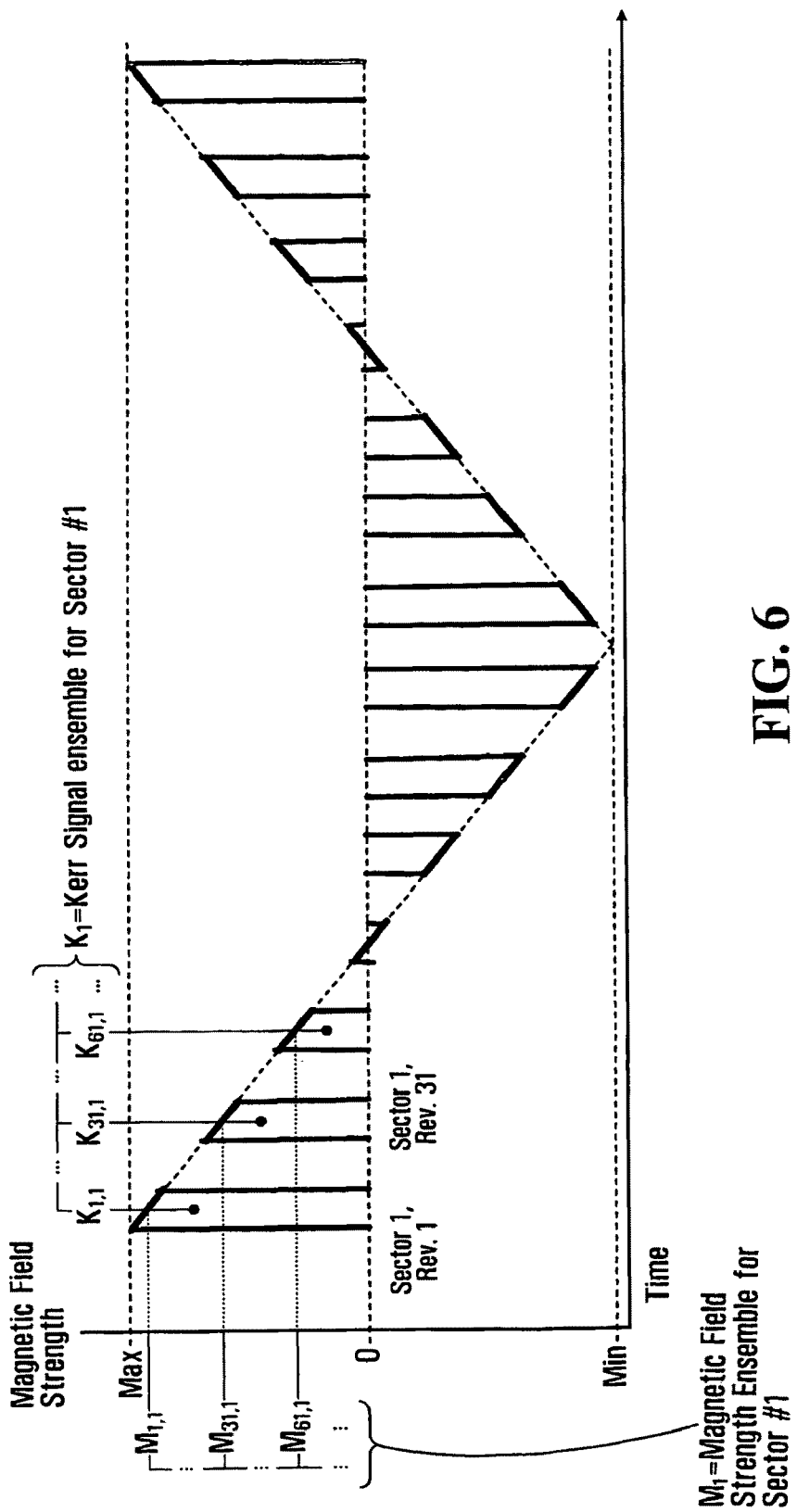
FIG. 6 illustrates identification of an ensemble of measurements corresponding to an individual sector of the magnetic disk.

It will be noted that gradually sweeping the applied magnetic field while spinning the magnetic disk 404 creates the effect, within each sector, of stepping the applied magnetic field with an average decrement (or increment) of 100 Oe per step and a duty cycle of $G_m/\pi D_t$ for the case shown in FIG. 4A or $D_m/\pi D_t$ for the case shown in FIG. 4B (where $D_m$ and $D_t$ are the diameters of, respectively, the magnetic poles 421A, 421B and the track under test). To present a simplified, yet realistic representation of the Kerr signal ensemble $K_1$ and magnetic field strength ensemble $M_1$ for sector #1, only a fraction of the total number of 400 revolutions of the magnetic disk 404 is represented in FIG. 6.

Figure 7:
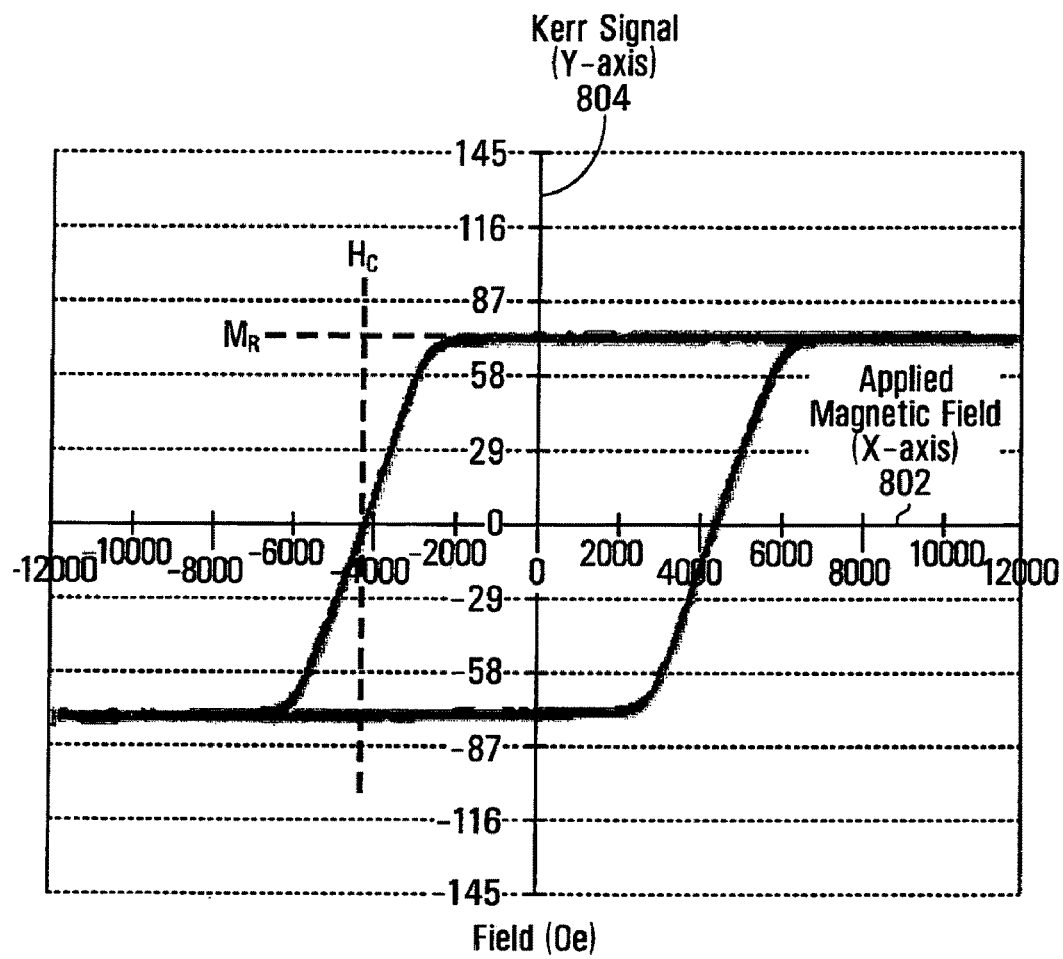
FIG. 7 shows derivation of remanence and coercivity from a hysteresis loop obtained from the ensemble of measurements corresponding to an individual sector of the magnetic disk.

Next, a magnetic property (such as remanence and/or coercivity) for a particular sector (e.g., sector #J) is determined by plotting the Kerr signal ensemble for the particular sector (namely, $K_J$) against the magnetic field strength ensemble for the particular sector (namely, $M_J$). With reference to FIG. 7, the Kerr signal measurement in milli-degrees for a particular sector on the track under test (Y-axis 804) was plotted against the applied magnetic field measurement in Oe (X-axis 802). The resulting plot takes the shape of a hysteresis loop since the Kerr signal measurement may be different at two different samples for which the magnetic field strength has the same value. Specifically, the Kerr signal measurement will depend on whether the applied magnetic field was increasing or decreasing at the time the measurement was taken.

Once the hysteresis loop for the particular sector is plotted, its coercivity and remanence may be determined. The coercivity (denoted $H_C$) for a sector can be determined as the value of the applied magnetic field at a Kerr signal (or magnetization value) of zero, while the remanence (denoted $M_R$) is determined as the Kerr signal (or magnetization value) at zero applied magnetic field. With respect to the example hysteresis loop illustrated in FIG. 7, the coercivity (identified here as HO for this particular sector can be determined to be around 4300 Oe while the remanence (identified here as $M_R$) as for this sector can be determined to be around 73 milli-degrees.

Advantageously, the above technique can be performed for any number of sectors on the track under test, based on the corresponding Kerr signal ensemble and magnetic field strength ensemble for each desired sector. All the ensembles are formed from the same time series of Kerr signal measurements $\{K(i)\}$ and the same time series of magnetic field strength measurements $\{M(i)\}$. In this way, the single application of a sweeping magnetic field while the magnetic medium rotates can be used to determine magnetic properties of multiple sectors of a track under test. This makes the process more efficient than having to separately apply the sweeping magnetic field to each point in each sector to be measured individually and in sequence.

The hysteresis loops for different sectors will be different, meaning that the coercivity and remanence of these sectors are correspondingly different and thus the values will form a distribution. In particular, the set of values representing remanance and coercivity of the sectors of the track under test can be depicted in graphical formats such as, but not limited to, tables, charts and/or graphs.

Figure 8A:
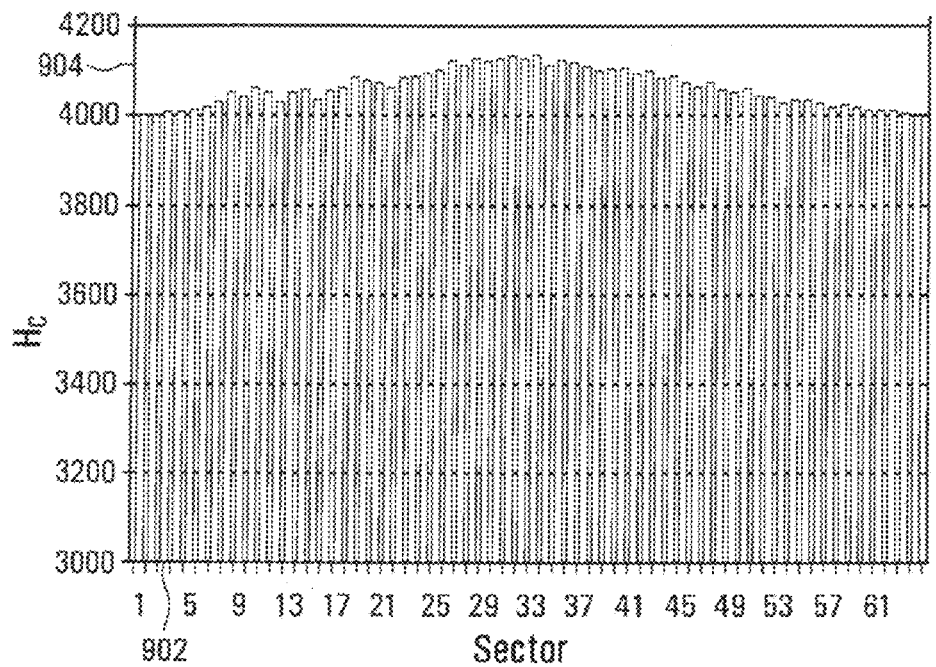
FIGS. 8A and 8B show alternate graphical representations of a particular magnetic property found to be exhibited by the various sectors of a magnetic disk as a result of testing using the test bed of FIG. 3.
Figure 8B:
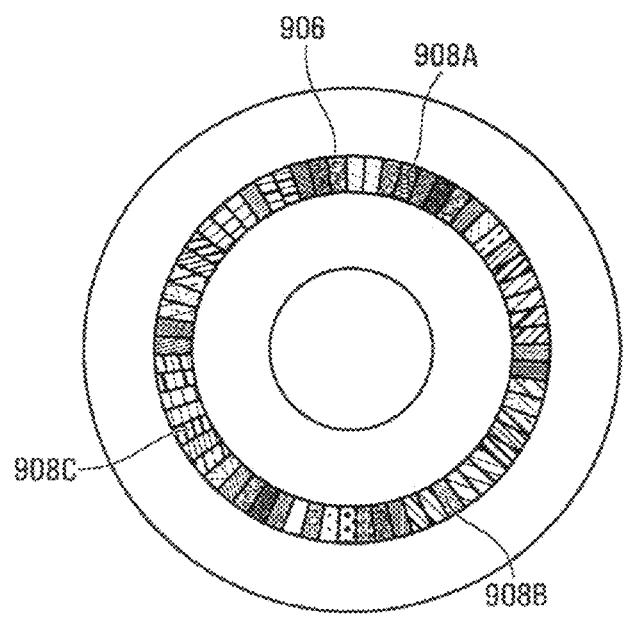

FIGS. 8A and 8B illustrate two sample graphical formats that could be used to depict the remanence and coercivity of a set of 64 sectors. In FIG. 8A, a possible distribution of the coercivity for each of the 64 sectors of a given track are plotted in a columnar graph. Specifically, a sector's coercivity in Oe (Y-axis 904) is plotted against the sector's ordinal number (X-axis 902). In a non-limiting example, this type of graph could be used to compare the coercivity found for sectors on a given track of a magnetic medium against a baseline to see if there is a difference relative to the baseline. In the affirmative, further investigations could be made to identify the reason for the disparity between the anomalous observed coercivity values and the baseline.

FIG. 8B shows the same distribution of the coercivity for plural sectors in a graphical format that schematically represents a track 906 of sectors 908A, 908B, 908C on a circular disk. In this format, ranges of values for the coercivity are associated with a specific color. For example, a coercivity between 3000 Oe and 3200 Oe (such as in sector 908A) may be set to be displayed in light blue, while a coercivity between 3201 Oe and 3500 Oe (such as in sector 908B) may be set to be displayed in green. In this way, the coercivity for multiple sectors of the track 906 can be viewed simultaneously, and anomalies can be identified based on the appearance of a specific color, hue or shading. This technique advantageously allows the rapid identification of sectors that are fall outside of predetermined maximum or minimum values. For example, the color red could be used to flag sectors on a track whose coercivity is either less than 2000 Oe or is greater than 6000 Oe, such as in sector 908C. Certain colors or shadings may be used to identify sectors whose coercivity may fall outside of the operational parameters necessary for equipment to properly effect read and write operations on the sectors in question.

While FIG. 8B shows the distribution of coercivity for a single track on a magnetic medium such as a disk, the same format could also be used to show the distribution of coercivity for multiple tracks on the medium.

It should be appreciated that the remanence can be converted from units of milli-degrees into units of ampere/m. More specifically, the relationship is $M=f \cdot \Phi$, where f is a factor dependent on the magnetic medium and $\Phi$ is the Kerr signal in milli-degrees, which is dependent on the magnetic medium and the optical configuration. It should be noted that calibration may be required to determine which precise value of f to use. However, relative values can be used to compare the remanence among different sectors of a track without necessarily having to compute the true values, thus avoiding the need for calibration.

As described previously, the optical beam system 411 generates the incident optical beam 412 continuously during a test, regardless of whether a measurement is currently being performed on the magnetic disk 404. In a variant of the method and apparatus described above, the optical beam system 411 generates the incident optical beam 412 only when a measurement is needed to be performed by the controller 433. The intermittent nature of the optical beam generated in this variant may reduce power consumption or extend the life of the components in the optical beam system 411.

As described previously, the time series of measurements $\{K(i)\}$, $\{M(i)\}$, $\{A(i)\}$ received by the controller 433 during a test undergoes post-processing to generate ensembles of measurements. Proper execution of this post-processing depends on knowledge of variables such as the number of sectors per track of the magnetic medium, the rotation speed of the magnetic medium, and the profile of the applied magnetic field. It is conceivable that many or all of these variables will be known well in advance, such as for a test bed that is pre-configured to only test disks used in a particular type of hard drive. In such a case, the various ensembles 610 can be built up from measurements taken in real-time, while the magnetic medium rotates.

Moreover, it should be appreciated that the magnetic field strength measurements M(i) can be predicted rather than measured. That is to say, the magnetic field driver 423, which has control over the magnetic field applied by the magnetic coil 422 via the gap 424, can estimate the applied magnetic field that it expects should exist across the gap 424 at various sample times and can feed this information (in digital form, for each sample "i") directly to the controller 433, without the need for a separate channel in the A/D converter 434.

Similarly, it should be appreciated that the spin angle measurements A(i) can be predicted rather than measured. That is to say, the controller 433, which has control over the spinning of the magnetic disk 404 by the spindle 431, can estimate the spin angle that it expects should be applied by the spindle 431 at various sample times and can feed this information (in digital form, for each sample "i") directly to the controller 433, without the need for a separate channel in the A/D converter 434.

In such a scenario, where both the magnetic field strength and the spin angle are predicted rather than measured, the only measurements taken by the test bed 420 would be the Kerr signal measurements K(i).

While specific embodiments of the present invention have been described and illustrated, it will be apparent to those skilled in the art that numerous modifications and variations

What is claimed is:

1. Apparatus for testing a magnetic medium, comprising:
a magnetic field generation sub-system configured to apply a magnetic field of a time-varying strength to a portion of the magnetic medium;
a light generation sub-system configured to direct a polarized optical beam towards the portion of the magnetic medium that is in the magnetic field, wherein the optical beam is reflected by a surface of the magnetic medium at a point of incidence in the magnetic field;
a motion sub-system configured to move the magnetic medium relative to the optical beam so as to cause the point of incidence to repeatedly traverse each of a plurality of sectors along a track on the surface of the magnetic medium, wherein the magnetic field generation sub-system and the motion sub-system cooperate to vary the strength of the magnetic field in synchronization with motion of the point of incidence along the track;
a measurement sub-system configured to obtain a series of Kerr signal measurements of the reflected optical beam as the point of incidence repeatedly traverses the sectors, each Kerr signal measurement being associated with (1) a corresponding one of the sectors in which the point of incidence was when the Kerr signal measurement was obtained and (2) a corresponding strength of the magnetic field at the time when the Kerr signal measurement was obtained; and
a control sub-system configured to group the series of Kerr signal measurements into ensembles such that the Kerr signal measurements in an individual ensemble are all associated with the same one of the sectors, the control sub-system being further configured to determine at least one magnetic property of at least one of the sectors from the Kerr signal measurements in the corresponding ensemble.

2. The apparatus defined in claim 1, wherein the magnetic medium is circular with a center and wherein motion sub-system comprises a spindle for rotating the magnetic medium about an axis passing through said center.

3. The apparatus defined in claim 2, wherein the motion sub-system further comprises a motion stage for translating the spindle so that the circular track containing the point of incidence corresponds to a specific track to be tested.

4. The apparatus defined in claim 1, wherein the light generation sub-system comprises a light source and a polarizer.

5. The apparatus defined in claim 4, wherein the light generation sub-system further comprises at least one mirror for directing an output of the light source through the polarizer.

6. The apparatus defined in claim 4, wherein the measurement sub-system comprises a polarization analyzer for admitting the reflected optical beam and a photodetector coupled to the polarization analyzer.

7. The apparatus defined in claim 6, wherein the polarization analyzer has an optical axis that is offset from an optical axis of the polarizer.

8. The apparatus defined in claim 6, wherein the optical beam detection unit further comprises an amplifier for amplifying an output of the photodetector.

9. The apparatus defined in claim 6, wherein the control sub-system comprises an analog-to-digital converter for converting an output of the photodetector into digital samples representative of said measurements and a memory for storing the digital samples.

10. The apparatus defined in claim 2, wherein the control sub-system comprises a controller that carries out grouping of said series of measurements into said ensembles based on a rate of rotation of the magnetic medium, a rate of obtaining said Kerr signal measurements and a profile that defines a variation of the strength of the applied magnetic field.

11. The apparatus defined in claim 10, wherein the control sub-system comprises a computing control panel that allows a user to set the profile that defines the variation of the strength of the applied magnetic field.

12. The apparatus defined in claim 1, wherein the control sub-system comprises a computing unit that implements instructions for driving a display unit to display graphical information indicative of the at least one magnetic property of the at least one of the sectors.

13. The apparatus defined in claim 12, wherein the computing unit further implements instructions for driving the display unit to simultaneously display graphical information indicative of at least one magnetic property of plural ones of the sectors.

14. The apparatus defined in claim 1, wherein the at least one magnetic property includes magnetic remanence.

15. The apparatus defined in claim 1, wherein the at least one magnetic property includes magnetic coercivity.

16. A method of testing a magnetic medium, comprising:
applying a magnetic field of a time-varying strength to a portion of the magnetic medium;
directing a polarized optical beam towards the portion of the magnetic medium that is in the magnetic field, wherein the optical beam is reflected by a surface of the magnetic medium at a point of incidence in the magnetic field;
moving the magnetic medium relative to the optical beam so as to cause the point of incidence to repeatedly traverse each of a plurality of sectors along a track on the surface of the magnetic medium, wherein the strength of the magnetic field is varied in synchronization with motion of the point of incidence along the track;
obtaining a series of Kerr signal measurements of the reflected optical beam as the point of incidence repeatedly traverses the sectors, each Kerr signal measurement being associated with (1) a corresponding one of the sectors in which the point of incidence was when the Kerr signal measurement was obtained and (2) a corresponding strength of the magnetic field at the time when the Kerr signal measurement was obtained; and
grouping the series of Kerr signal measurements into ensembles such that the Kerr signal measurements in an individual ensemble are all associated with the same one of the sectors; and
determining at least one magnetic property of at least one of the sectors from the Kerr signal measurements in the corresponding ensemble.

17. The method defined in claim 16, comprising:
obtaining a series of field strength measurements of the applied magnetic field, the field strength measurements being obtained in synchronism with the Kerr signal measurements;
grouping the series of field strength measurements into ensembles such that the field strength measurements in an individual ensemble are those obtained while the point of incidence was in a corresponding one of the sectors;

determining the at least one magnetic property of the at least one of the sectors from the Kerr signal measurements in the corresponding ensemble of Kerr signal measurements and from the field strength measurements in the corresponding ensemble of field strength measurements.

18. The method defined in claim 17, wherein determining the at least one magnetic property of the at least one of the sectors comprises:
obtaining a hysteresis loop by plotting the Kerr signal measurements in the corresponding ensemble of Kerr signal measurements against the field strength measurements in the corresponding ensemble of field strength measurements; and
deriving the at least one magnetic property from the hysteresis loop.

19. The method defined in claim 18, wherein the at least one magnetic property includes magnetic remanence.

20. The method defined in claim 18, wherein the at least one magnetic property includes magnetic coercivity.

21. The method defined in claim 16, wherein said moving comprises rotating, wherein each of said sectors is exposed to a pulsed magnetic field with a period corresponding to the time taken by the magnetic medium to effect one revolution.

22. The method defined in claim 16, wherein the Kerr signal measurements are indicative of an angle of polarization rotation relative to a reference orientation in an absence of the magnetic field.

23. The method defined in claim 16, wherein to obtain the Kerr signal measurements from the reflected optical beam, the reflected optical beam is processed by a polarization analyzer and a photodetector.

24. The method defined in claim 23, further comprising sampling an output of the photodetector to obtain the Kerr signal measurements.

25. The method defined in claim 23, further comprising sampling an amplified output of the photodetector to obtain the Kerr signal measurements.

26. The method defined in claim 25, wherein said sampling is carried out at a sampling rate, wherein said grouping is carried out as a function of the sampling rate.

27. The method defined in claim 26, wherein said moving comprises rotating, wherein said grouping is carried out also as a function of a speed at which the magnetic medium rotates.

28. The method defined in claim 27, wherein said grouping is carried out also as a function of an arc length of each of said sectors.

29. The method defined in claim 28, further comprising providing a trigger signal to indicate a new revolution of the magnetic medium, wherein said grouping is carried out also as a function of when said trigger signal is received.

30. The method defined in claim 27, further comprising providing a clock signal synchronized with the revolutions of the magnetic medium, wherein said sampling is synchronized with the clock signal.

31. The method defined in claim 30, wherein applying the magnetic field comprises sweeping the strength of the magnetic field over a range of values in accordance with a profile.

32. The method defined in claim 31, wherein the profile is set by a user.

33. The method defined in claim 16, wherein the Kerr signal measurements are indicative of a manifestation of a magneto optic Kerr effect at the point of incidence.

34. The method defined in claim 16, wherein each measurement in the ensemble of Kerr signal measurements corresponding to a specific sector is an average of a plurality of samples of a Kerr signal taken during a single traversal of the specific sector by the point of incidence.

35. The method defined in claim 33, further comprising as a prior step, translating the magnetic disk so that the circular track containing the point of incidence corresponds to a specific track to be tested.

36. The method defined in claim 35, further comprising receiving knowledge from a user of the track to be tested.

37. The method defined in claim 36, further comprising simultaneously graphically conveying at least one magnetic property of at least two of the sectors.

38. The method defined in claim 16, wherein said directing is intermittent so that the optical beam is turned off and then on again between the obtaining of consecutive Kerr signal measurements.

39. Apparatus for testing a magnetic medium, comprising:
means for applying a magnetic field of a time-varying strength to a portion of the magnetic medium;
means for directing a polarized optical beam towards the portion of the magnetic medium that is in the magnetic field, wherein the optical beam is reflected by a surface of the magnetic medium at a point of incidence in the magnetic field;
means for moving the magnetic medium relative to the optical beam so as to cause the point of incidence to repeatedly traverse each of a plurality of sectors along a track on the surface of the magnetic medium, wherein the means for applying the magnetic field and the means for moving the magnetic medium cooperate to vary the strength of the magnetic field in synchronization with motion of the point of incidence along the track;
means for obtaining a series of Kerr signal measurements of the reflected optical beam as the point of incidence repeatedly traverses the sectors, each Kerr signal measurement being associated with (1) a corresponding one of the sectors in which the point of incidence was when the Kerr signal measurement was obtained and (2) a corresponding strength of the magnetic field at the time when the Kerr signal measurement was obtained;
means for grouping the series of Kerr signal measurements into ensembles such that the Kerr signal measurements in an individual ensemble are all associated with the same one of the sectors; and
means for determining at least one magnetic property of at least one of the sectors from the Kerr signal measurements in the corresponding ensemble.

40. Non-transitory computer-readable media containing instructions which, when executed by a computing device, cause the computing device to implement a method that comprises:
receiving a time series of measurements, each measurement representative of a manifestation of a magneto-optic Kerr effect within an individual sector from among a plurality of sectors of a magnetic medium at an associated strength of an applied magnetic field, the measurements associated with different sectors being time-interleaved;
grouping the time series of measurements into ensembles, the measurements in each one of the ensembles being associated with a respective one of the sectors;
determining at least one magnetic property of plural ones of the sectors from measurements in the corresponding ones of the ensembles; and
outputting an indication of said at least one magnetic property of said plural ones of the sectors.

41. The non-transitory computer-readable media defined in claim 40, wherein said outputting comprises causing simultaneous graphical conveyance of the at least one magnetic property of said plural ones of the sectors.

* * * * *